United States Patent [19]

Venturello et al.

[11] Patent Number: 5,026,911

[45] Date of Patent: Jun. 25, 1991

[54] PROCESS FOR OXIDIZING SATURATED PRIMARY AMINES TO OXIMES

[75] Inventors: Carlo Venturello; Rino D'Aloisio, both of Novara, Italy

[73] Assignee: Istituto Guido Donegani S.p.A., Milan, Italy

[21] Appl. No.: 514,218

[22] Filed: Apr. 25, 1990

[30] Foreign Application Priority Data

Apr. 27, 1989 [IT] Italy ................................ 20293 A/89

[51] Int. Cl.$^5$ ............................................ C07C 249/04
[52] U.S. Cl. ..................................... 564/253; 564/267; 564/268
[58] Field of Search ................ 564/253, 262, 267, 268

[56] References Cited

U.S. PATENT DOCUMENTS

| | | | |
|---|---|---|---|
| 3,960,954 | 1/1976 | Russell et al. | 564/268 |
| 4,337,358 | 6/1982 | Armor | 564/268 |
| 4,504,681 | 3/1985 | Armor | 564/268 |
| 4,560,797 | 12/1985 | Yamanis et al. | 564/268 |

FOREIGN PATENT DOCUMENTS 47-25324  7/1972  Japan ................................ 564/268

OTHER PUBLICATIONS

Raffia et al., Chem. Abst., vol. 111, #9251a (1989).
Padovan et al., Chem. Abst., vol. 110, #175517r (1989).
Sheldon et al., *Metal-Catalyzed Oxidations of Organic Compounds*, pp. 49–58 (1981).
Patai, *The Chemistry of Peroxides*, pp. 463–467 (1983).

*Primary Examiner*—James H. Reamer
*Attorney, Agent, or Firm*—Stevens, Davis, Miller & Mosher

[57] ABSTRACT

The invention relates to a process for preparing oximes starting from saturated primary (cyclo)aliphatic amines optionally substituted by groups which are inert under the reaction conditions, by reacting the saturated primary amine with oxygen, the reaction being conducted in the liquid phase in the presence of at least a catalyst based on compounds belonging to Group IV B of the Periodic System, thereby obtaining the corresponding aliphatic and cycloaliphatic oximes.

14 Claims, No Drawings

PROCESS FOR OXIDIZING SATURATED PRIMARY AMINES TO OXIMES

BACKGROUND OF THE INVENTION

1. Field of the Invention

The present invention relates to a process for preparing aliphatic and cycloaliphatic oximes obtained by reacting in the liquid phase the corresponding saturated primary aliphatic or cycloaliphatic amine with oxygen in the presence of catalysts based on compounds of metals of Group IV B of the Periodic System (titanium, zirconium, hafnium).

The (cyclo)aliphatic oximes so obtained are products, which have "per se" useful applications, for example as oxidation inhibitors, or they represent interesting intermediates for the production of amides with corresponding wide applicative possibilities.

In particular, when the amine is cyclohexylamine, the resulting cyclohexanone oxime can be further converted to the corresponding cyclic amine, or epsilon-caprolactam.

The caprolactam represents the starting monomer for obtaining nylon 6.

2. Discussion of the Prior Art

Already known is the oxidation reaction of saturated aliphatic or cycloaliphatic primary amines (cyclohexylamine), having a C—H linkage in alpha position with respect to the aminic group, with hydrogen peroxide to obtain oximes, by operating in the presence of catalysts based on molybdenum, tungsten, uranium, or with organic hydroperoxides, by operating in the presence of catalysts based on titanium, molybdenum, tungsten and vanadium in the organic phase.

Nevertheless, the use of the abovesaid oxidizing agents is expensive and, in the case of the utilization of an organic hydroperoxide, further complications connected with the separation, purification and the like can occur due to the presence, in the final reaction mixture, of by-products (alcohols) deriving from the reduction of the hydroperoxide.

To these drawbacks, the known operative risks related to the handling of peroxide compounds are to be added.

On the other hand it is also known to prepare oximes from saturated (cyclo)aliphatic primary amines of the abovesaid type by using oxygen as an oxidant in the presence of solid catalysts based on SiO$_2$ gel, gamma Al$_2$O$_3$, optionally associated with tungsten oxides, operating in the gas phase.

This is a process which involves relatively severe operative conditions due to the gas phase (temperatures approximately ranging from 120° C. to 250° C., etc.).

On the other hand it was assumed so far that metals such as titanium should generally be only efficient activators of peroxide compounds.

DISCLOSURE OF THE INVENTION

Conversely, it has now surprisingly been found by the Applicant, and forms the object of the present invention, that the oxidation reaction of saturated (cyclo)aliphatic primary aminic substrates to oximes can be carried out by operating with oxygen in the liquid phase and using catalysts based on compounds of metals belonging to Group IV B of the Periodic System.

Thus, according to the present invention, aliphatic and cycloaliphatic oximes, in which the (cyclo)aliphatic residue can be optionally substituted by groups which are inert under the reaction conditions and can contain from 2 to 15 carbon atoms, are prepared by reaction of the corresponding saturated (cyclo)aliphatic primary amine, containing a C—H linkage in alpha position with respect to the aminic group, with oxygen, said reaction being conducted in the liquid phase in the presence of a catalyst consisting of at least a compound of a metal belonging to Group IV B of the Periodic System.

The saturated (cyclo)aliphatic amine, which is the starting substrate, has the formula:

in which R' represents a straight or branched alkyl group, R" represents a hydrogen atom or a straight or branched alkyl group, the same or different from R', or R' and R", taken together, give rise to a cyclomethylene ring, while the total of the carbon atoms contained in R' and R" amounts up to 15.

The oxidation reaction can be schematically represented as follows:

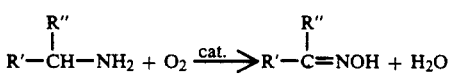

where R' and R" are the same as defined hereinabove.

As mentioned above, the process object of the present invention is conducted by operating in the liquid phase consisting of the saturated primary aminic substrate which is utilized or of a solution thereof, in the presence of the catalyst based on compounds of the metals belonging to Group IV B of the Periodic System (Ti, Zr, Hf), which will be better defined hereinafter.

The starting saturated primary aminic substrate can be substituted by any saturated primary aminic structure of formula (I) containing from 2 to 15 carbon atoms, as is defined hereinbefore, also substituted by groups, which are inert under the oxidation conditions, for example lower alkyls C$_1$-C$_4$ etc. Besides cyclohexylamine, also cyclopentylamine, heptylamine, cyclododecylamine etc. have proved to be effective substrates.

The catalysts of the present invention are generally definable as compounds based on Ti, Zr, Hf (Group IV B of the Periodic System) in the form of salts, oxides, the latter optionally associated with SiO$_2$, or of metallorganic compounds, these being at least partially soluble in the organic reaction medium consisting of the aminic substrate "per se" or, as an alternative, of the substrate dissolved in a proper solvent, as will be defined hereinafter.

When a metallorganic compound is utilized, the process, object of the present invention, is conducted in the presence of at least a compound selected from the metallorganic compounds having formula (II):

wherein m represents an integer ranging from 1 to 4; n represents an integer ranging from 0 to 4, provided that m ≧ n; R represents one or, when m is other than 1, more hydrocarbyl residues like or different from one another also containing heteroatoms and/or inert functional groups, or R represents the corresponding acyl groups; M represents a metal selected from Ti, Zr and Hf; X represents a halogen, CN, CNS, a (cyclo)alkoxyl group, an aryloxy group, an acyloxy group, or two symbols X taken together represent

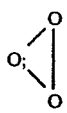

in particular, R represents one, or when m is other than 1, more $C_1$-$C_{14}$ (cyclo)aliphatic, $C_6$-$C_{14}$ (hetero)aromatic residues, like or different from each other, also substituted and/or interrupted by groups which are inert under the reaction conditions, such as alkyl groups, alkoxyl groups, CO, $NH_2$, OH groups, halogen atoms, or R represents acyl residues derived from the corresponding (cyclo)aliphatic and (hetero) aromatic carboxylic acids; M represents a titanium or zirconium atom; the group or groups X represent acyloxy groups derived from carboxylic acids as defined above, $C_1$-$C_{14}$ (cyclo)alkoxyl groups, $C_6$-$C_{14}$ (hetero)aryloxy groups, fluorine, chlorine, bromine, CN, CNS, and two symbols X taken together give rise to group=0.

More in particular, R consists of straight or branched $C_1$-$C_5$ alkyl groups, phenyl, naphthyl, indenyl, anisyl, cyclopentadienyl, acyl, benzoyl groups; X consists of $R_1$—COO—alkanoyloxy groups, wherein $R_1$ is a $C_1$-$C_5$ alkyl, $C_6H_5COO$—benzoyloxy groups, $C_1$-$C_5$ alkoxyl (methoxy, butoxy, etc.) groups, phenoxy groups; of halogen atoms (Cl, Br); M consists of a titanium or zirconium atom.

The following titanium and zirconium organic compounds comprised in formula I have proved to be active catalysts: titanium ethylate, n-butylate, isopropylate, diisopropyloxydiacetylacetonate, titanyl 8-hydroxyquinolinate, titanium acetylacetonate, bis(cyclopentadienyl) titanium dichloride, bis(cyclopentadienyl) titanium dibutylate, bis(cyclopentadienyl) titanium diphenate, bis(cyclopentadienyl) titanium dinaphthoate, bis(cyclopentadienyl) titanium diphenate, bis(1,1-dinaphthyl-2,2'-diyl) orthotitanate, alpha-naphthyl titanium tributylate, indenyl titanium tributylate, dicyclopentadienylmethyl titanium chloride, zirconium ethylate, zirconium acetylacetonate, di-n.butyl-di-(2,6-di-t.butyl-p.cresyl) titanate, n.butyl-trioleyl titanate, tetra-o.cresyl titanate, titanium naphthenate, titanium stearate, titanium caproate, bis-acetate-titanium dichloride.

As mentioned above, the catalyst can be also selected from the salts and the oxides of the above said metals belonging to Group IV B of the Periodic System, while the oxides can be also utilized in an associated form, for example carried on $SiO_2$, for example such as $TiO_2$/$SiO_2$.

$TiO_2$/$SiO_2$, $TiO_2$, its saline derivatives such as titanyl sulphate, $TiCl_4$, etc. have proved to be active catalysts.

The catalyst, as mentioned above, can be also carried, for example, on carriers such as $SiO_2$, $Al_2O_3$, coal, etc., which are utilized according to conventional techniques.

Advantageous results were obtained by using the $TiO_2$/$SiO_2$ catalyst prepared according the procedure disclosed in published European Patent Application No. 347,926.

Said Application discloses solid compositions consisting of silicon, titanium and oxygen, chemically combined with each other, wherein the titanium amount, expressed as $TiO_2$, ranges from 1 to 95% by weight with respect to the whole composition, and wherein the XR diffractogram of said composition (obtained by means of the Kα radiation of copper) shows, in the (2 θ) range from 10° to 40°, a smooth-trend line.

As already mentioned, it is possible to use $TiO_2$/$SiO_2$ catalysts in the form of titanium silicalites. Titanium silicalites are well known crystalline products having a zeolitic structure anc containing silicon, titanium and oxygen, such as those described in British patents Nos. 2,071,071; 2,024,790; U.S. Pat. Nos. 4,410,501; 4,480,135 and patents EP No. 208,311 and EP No. 299,430.

The catalyst based on salts, oxides etc., as defined above, is utilized in the conventional physical form, for example as granules, or in the form of powders in a suspension etc., operating in a heterogeneous phase.

The process object of the present invention is conducted in the liquid phase, which consists of the saturated primary amine substrate such as is defined (I) if it is in the liquid state, or preferably dissolved in an organic solvent such as acetonitrile, dioxane, dimethoxyethane, diglyme, $C_1$-$C_{10}$ alcohols (tert.butanol), aromatic hydrocarbons such as toluene, dimethylformamide, dimethylsulphoxide, lower trialkylamines (triethylamine). It is also possible to use water.

When it is operated in the presence of a solvent, the substrate concentration preferably ranges from 10% to 15% by weight, approximately.

Usually, the process of the present invention is conducted in one step by directly charging into an autoclave, the saturated primary aminic solvent as such, if it is liquid, or in solution, the catalyst and $O_2$ in the gaseous state, under pressure.

The pressure employed generally ranges from 3 to 50 atmospheres, approximately, and preferably from 15 to 35 atmospheres, approximately. Furthermore, it is operated at a temperature higher than 50° C., usually in the range from 50° to 150° C., preferably from 90° to 130° C., approximately.

Gaseous molecular oxygen is utilized also in the form of air or of mixtures with inert gases.

The catalyst is utilized, according to the present invention, in an amount ranging from 0.005 to 0.3 gram atoms of metal (Ti, Zr, Hf) contained in the utilized compound for each mole of substrate.

The reaction times generally range—depending on the operative conditions—from 2 to 4 hours, approximately.

The oxime separation can be conducted conventionally.

The invention will be described in detail in the following examples, which are given, however, for illustrative purposes and are not to be considered as a limitation of the invention.

EXAMPLE 1

Into a stainless steel autoclave having a 100 ml volume, equipped with magnetic stirrer, heating system, ramps for charging and discharging the gases, there were introduced:
2.97 g (3.43 ml) of cyclohexylamine (about 30 millimols),
12 ml of diglyme,
0.4 g of tetramethyl orthotitanate (about 1.75 millimols).

The autoclave was closed and about 30 kg/cm² gauge of $O_2$ were introduced; the whole was heated to 100° C. and was reacted during 4 hours under intense stirring.

After cooling, the residual pressure was discharged, the autoclave was opened, the mass was diluted with ethyl ether, filtration was effected to remove the catalyst, and the filtrate was analyzed by gas chromatography.

A selectivity in cyclohesanone oxime equal to about 50% was obtained, the cyclohexylamine conversion being of 62%.

EXAMPLE 2

Example 1 was repeated, using 15 ml of diethylene glycol dimethyl ether (diglyme) and a temperature of 110° C.

A selectivity in cyclohexanone oxime equal to 44% and a cyclohexylamine conversion of 81% were obtained.

EXAMPLE 3

Example 1 was repeated, using tert.butanol as a solvent and a temperature of 95° C.

A selectivity in oxime equal to 51.8% was obtained, the cyclohexylamine conversion being of 63%.

EXAMPLE 4

Example 1 was repeated, using an $O_2$ pressure of 20 $kg/cm^2$ gauge instead of 30 $kg/cm^2$ gauge.

A selectivity in oxime equal to 50% was obtained, the amine conversion being of 48.3%.

EXAMPLE 5

Example 1 was repeated, using 12 ml of $H_2O$ as a solvent and a temperature of 120° C. for 2 hours.

A selectivity in oxime equal to 16% was obtained, the amine conversion being of 21%.

EXAMPLE 6

Example 1 was repeated, using 12 ml of dimethylformamide as a solvent and a temperature of 90° C. for 3 hours.

A selectivity in oxime equal to 44.3% was obtained, the amine conversion being of 68.2%.

EXAMPLE 7

Example 6 was repeated, using $CH_3CN$ as a solvent.

A selectivity in oxime equal to 15% was obtained, the amine conversion being of 28.8%.

EXAMPLE 8

Example 6 was repeated, using triethylamine as a solvent.

A selectivity in oxime equal to 37.3% was obtained, the amine conversion being of 37.5%.

EXAMPLE 9

Example 1 was repeated, using 0.415 g (1.75 millimols) of bis-acetate titanium dichloride as a catalyst.

A selectivity in oxime equal to 35% was obtained, the amine conversion being of 96%.

EXAMPLE 10

Example 1 was repeated, using tert.butanol as a solvent and 0.855 g (1.75 millimols) of zirconium tetra-acetylacetonate as a catalyst.

A selectivity in oxime equal to 25% was obtained, the amine conversion being of 92%.

EXAMPLE 11

Preparation of the Titanium Silicalite Catalyst 544 g of tetraethyl orthosilicate were introduced into a flame resistant Pyrex glass flask equipped with a stirrer and maintained in an inert nitrogen atmosphere. 24 g of titanium tetraisopropylate were then added and subsequently 1,200 g of an aqueous solution of tetrapropylammonium hydroxide at 20% by weight were gradually added (by dropping). The mixture was maintained under stirring for 1 hour at room temperature, then it was allowed to rest, always at room temperature, for 1 hours. The temperature was gradually raised up to 78° C. to remove ethyl alcohol, and then it was brought to 98° C. to remove isopropyl alcohol. The removal of the alcohols which generate in the course of the reaction, was carried out, under stirring, in 5 hours. After cooling, the volume of the liquid was brought to 2 liters by addition of deionized water and the (homogeneous and opalescent) solution was transferred into an autoclave equipped with stirrer, where the hydrothermam synthesis was effected at 175° C. in a 10-day time under an autogenous pressure.

The reaction mixture was cooled and filtered, and the solid product was repeatedly washed until obtaining a neutral pH, whereafter it was dried at 120° C. for 15 hours. The dried product was lastly calcined at 420° C. for 10 hours.

The calcined product was placed into a beaker and mixed with an aqueous solution prepared by pouring 100 ml of hydrogen peroxide (at 30% by weight) along with 1,000 ml of dilute sulphuric acid (at 5% by weight); mixing was continued for two hours at 70° C., then the liquid was separated by decantation. This operation was repeated twice with fresh solutions, and after the last acid washing a filtration was carried out, which was followed by a long washing with deionized water (until neutral pH), and the product was dried at 120° C. for 15 hours; lastly, the product was calcined at 550° C. for 2 hours. On analysis, the content of Ti as such was equal to 0.9%.

EXAMPLE 12

Example 1 was repeated, using 7 ml of diglyme instead of 12 ml, a temperature of 120° C. and 1 g of titanium silicalite in powder, prepared as in example 11, as a catalyst.

A selectivity in oxime equal to 30% was obtained, the amine conversion being of 36.5%.

EXAMPLE 13

Preparation of the $TiO_2$ Catalyst

To 100 g of titanium tetraisopropylate there were added, dropwise and under stirring, 100 ml of distilled water. The mass was maintained under stirring for 4 hours at room temperature.

After filtration and careful washing with water, the precipitate was dried for 16 hours at 120° C. and subsequently at 200° C. for 2 hours.

The resulting product had a specific surface of 255 $m^2/g$.

EXAMPLE 14

Example 12 was repeated, using 0.4 g of $TiO_2$ in powder prepared in example 13 as a catalyst.

A selectivity in oxime equal to 27.9% was obtained, the amine conversion being of 35%.

EXAMPLE 15

Example 1 was repeated, using 2.55 g (about 30 millimols) of cyclopentylamine as a substrate, 12 ml of tert.butanol as a solvent and a reaction time of 3 hours.

A selectivity in cyclopentanone oxime equal to 25.1% was obtained, the conversion of cyclopentylamine being of 96%.

EXAMPLE 16

Example 15 was repeated, using 3.46 g (30 millimols) of heptylamine as a substrate.

A selectivity in oxime equal to 22.4% was obtained, the heptylamine conversion being of 50.6%.

EXAMPLE 17

Preparation of the $TiO_2/SiO_2$ catalyst according to published European Patent Application No. 347,926.

50 g of an amorphous microspheroidal silica having a surface area of 408 m$^2$/g and a pore volume equal to 2.10 cm$^3$/g were calcined at 300° C. for 1 hour and subsequently impregnated with 115 cm$^3$ of a solution consisting of 35 cm$^3$ of tetraisopropyl-orthotitanate and of 80 cm$^3$ of isopropyl alcohol, which had been previously dehydrated on a molecular sieve (Zeolite 4A). The so impregnated silica was allowed to rest during 4 hours at room temperature; then it was dried at 120° C. for 16 hours. The resulting catalyst contained 16.4% by weight of titanium, expressed as $TiO_2$.

EXAMPLE 18

Example 1 was repeated by using 12 ml of ter. butanol as a solvent, a temperature of 110° C., a reaction time of 3 hours and 1 g of $TiO_2/SiO_2$, prepared in example 17 in the form of powder, as catalyst.

A selectivity of cyclohesanone oxime equal to 48.5% was obtained; the cyclohexylamine conversion being of 53%.

What is claimed is:

1. A process for the manufacture of aliphatic or cycloaliphatic oximes comprising:

reacting the corresponding saturated aliphatic or cycloaliphatic primary amine, containing a C—H bond in the alpha position with respect to the aminic group, with oxygen;

wherein the reaction is carried out in the liquid phase, at a temperature of 50°–150° C. and a pressure of 3–50 atmospheres, in the presence of a catalyst selected from the group consisting of titaniumsilicalites, and the salts, oxides and metallorganic compounds of a metal selected from the group consisting of Ti, Zr and Hf, the amount of metal being from 0.005 to 0.300 mol per mol of amine substrate;

wherein the concentration of the substrate in the solvent is from 10% to 40% by weight and the solvent is selected from the group consisting of water, an excess of amine substrate acetonitrile, dioxane, dimethoxyethane, diglyme, $C_1$–$C_{10}$ alcohols, aromatic hydrocarbons, dimethylformamide, dimethylsulphoxide and triethylamine, and mixtures thereof.

2. The process according to claim 1, wherein the saturated (cyclo)aliphatic primary amine is of the formula:

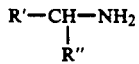

wherein R' represents straight or branched alkyl, R" represents hydrogen or straight or branched alkyl, or R' and R", taken together form a cyclomethylene ring, while the total number of carbon atoms present in R' and R" is 15.

3. The process according to claim 1, wherein the starting cycloaliphatic primary amine, which is unsubstituted or substituted by groups which are inert to the reaction, is selected from the group consisting of cyclohexylamine, cyclopentylamine, heptylamine, and cyclododecylamine.

4. The process according to claim 1 wherein the catalyst consists essentially of a metallorganic compound having the formula (II):

wherein m represents an integer from 1 to 4; n represents an integer from 0 to 4 such that m >n; R represents one or, when m is greater than 1, more hydrocarbyl residues which may be the same or different, which also contain heteroatoms and/or inert functional groups, or R represents the corresponding acyl groups; M represents a metal selected from the group consisting of Ti, Zr and Hf; X represents halogen, CN, CNS, (cyclo)alkoxyl, aryloxy, acyloxy, or two X's taken together represent

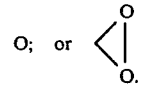

5. The process according to claim 4, wherein the catalyst consists essentially of a compound having the formula (II) in which: R represents one or, when m is greater than 1, more $C_1$–$C_{14}$ (cyclo)aliphatic, $C_6$–$C_{14}$ (hetero)aromatic residues which may be the same or different, which may be substituted and/or interrupted by groups which are inert under the reaction conditions, or R represents acyl residues derived from the corresponding (cyclo)aliphatic and (hetero)aromatic carboxylic acids; M represents titanium or zirconium; X represents acyloxy derived from said carboxylic acids, $C_1$–$C_{14}$ (cyclo)alkoxyl, $C_6$–$C_{14}$ (hetero)aryloxy, fluorine, chlorine, bromine, CN, or CNS, and two X's taken together represent O.

6. The process according to claim 4, wherein the catalyst consists essentially of a compound having the formula (II) in which: R represents straight or branched $C_1$–$C_5$ alkyl, phenyl, napthyl, indenyl, anisyl, cyclopentadienyl, or $R_1$—COO-alkanoyloxy, in which $R_1$ is $C_1$–$C_5$ alkyl or benzoyl; X represents $C_1$–$C_5$ alkanoyloxy, $C_6H_5$—COO-benzoyloxy, $C_1$–$C_5$ alkoxyl, phenyloxy Cl or Br; and M represents titanium or zirconium.

7. The process according to claim 1, wherein the catalyst is selected from the group consisting of titanium ethylate, n-butylate, isopropylate, diisopropyloxydiacetyl acetonate, titanyl 8-hydroxy-quinolinate, titanium acetonate, bis(cyclopentadienyl) dichloride, bis(cyclopentadienyl) titanium diphenate, bis(cyclopentadienyl) titanium diphenate, bis(cyclopentadienyl) titanium dinaphthoate, bis(1,1-binaphthyl-2,2'-diyl)-orthotitanate, alpha-naphthyl titanium tributylate, indenyl titanium tributylate, dicyclopentadienyl methyl titanium chloride, zirconium ethylate, zirconium acetylacetonate, di-n-butyl-di-(2,6-de-t.butyl-p.cresyl) titanate, n.butyl-trioleyl titanate, tetra-o.cresyl titanate, titanium naphthenate, titanium stearate, titanium caproate, and bis-acetate-titanium dichloride.

8. The process according to claim 1 wherein the catalyst consists essentially of a compound selected from the group consisting of $TiO_2$, titanyl sulphate, titanium tetrachloride and titanium silicalite.

9. The process according to claim 1, wherein the catalyst is carried on and/or associated with $SiO_2$, $Al_2O_3$ or coal.

10. The process according to claim 1, wherein the catalyst consists of a composition of $TiO_2/SiO_2$ chemically combined, wherein $TiO_2$ ranges from 1 to 95% by weight with respect to the whole composition, and the XR diffractogram of said composition (obtained by means of the $K\alpha$ radiation of copper) shows, in the ($2\theta$) range from 10° to 40°, a smooth-trend line.

11. The process according to claim 1, wherein the oxygen is introduced in the form of air or in an admixture with inert gases.

12. The process of claim 1, wherein the pressure is from 15 to 35 atmospheres.

13. The process of claim 1, wherein the temperature is from 90° to 130° C.

14. A process according to claim 5, wherein the inert groups are selected from the group consisting of alkyl, lower alkoxyl, CO, $NH_2$, OH and halogen.

* * * * *